United States Patent [19]

Walba et al.

[11] Patent Number: 4,835,295

[45] Date of Patent: May 30, 1989

[54] FERROELECTRIC LIQUID CRYSTAL COMPOUNDS AND COMPOSITIONS

[75] Inventors: David M. Walba; Homaune A. Razavi, both of Boulder, Colo.

[73] Assignee: The University of Colorado Foundation, Inc., Boulder, Colo.

[21] Appl. No.: 99,074

[22] Filed: Sep. 21, 1987

[51] Int. Cl.[4] .................. C07D 303/04; C07D 303/08; C07D 303/14

[52] U.S. Cl. .................... 549/557; 549/561; 549/563; 252/299.61; 252/299.67; 350/350 S

[58] Field of Search ........................ 549/561, 563, 557

[56] References Cited

U.S. PATENT DOCUMENTS

| | | | |
|---|---|---|---|
| 4,556,727 | 12/1985 | Walba | 560/72 |
| 4,638,073 | 1/1987 | Walba et al. | 549/556 |
| 4,695,650 | 9/1987 | Walba et al. | 560/109 |

OTHER PUBLICATIONS

Walba et al. (1986) J. Amer. Chem. Soc. 108:5210–5221.
Walba et al. (1986) J. Amer. Chem. Soc. 1087424–7425.

Primary Examiner—Glennon H. Hollrah
Assistant Examiner—S. P. Treanor
Attorney, Agent, or Firm—Greenlee and Associates

[57] ABSTRACT

Chiral, nonracemic compounds of the general formula:

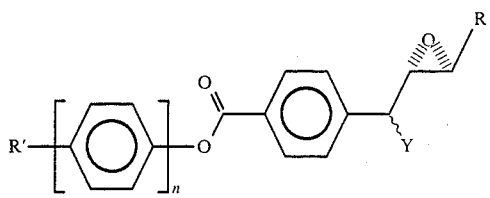

wherein n=1 or 2, Y is a hydrogen, fluorine, chlorine or bromine atom, R' is an alkyl or alkoxy group having three to fifteen carbons, and R is an alkyl group having three to fifteen carbons, which are useful as ferroelectric liquid crystal components having high polarization are described. Also described are compounds of the same general formula in which X is OH, which are useful as synthetic intermediates in the preparation of the FLC components of the present invention.

39 Claims, No Drawings

FERROELECTRIC LIQUID CRYSTAL COMPOUNDS AND COMPOSITIONS

This invention was made with partial support of the United States Government under Grant No. DMR-86-11192 awarded by the National Science Foundation and by the Office of Naval Research. The United States Government has certain rights in this invention. International Business Machines (IBM) also provided partial support for this work and has certain rights in this invention.

FIELD OF THE INVENTION

The present invention relates to ferroelectric liquid crystals useful in electro-optical and display device applications.

BACKGROUND OF THE INVENTION

Liquid crystals have found use in a variety of electro-optical and display device applications, in particular those which require compact, energy-efficient, voltage-controlled light valves such as watch and calculator displays. These devices are based upon the dielectric alignment effects in nematic, cholesteric and smectic phases of the liquid crystal compound in which, by virtue of dielectric anisotropy, the average molecular long axis of the compound takes up a preferred orientation in an applied electric field. Since the coupling to an applied electric field by this mechanism is rather weak, the resultant electro-optical response time may be too slow for many potential applications.

Liquid crystal displays have a number of unique characteristics, including low voltage and low power of operation, which makes them perhaps the most promising of the non-emissive electro-optical display candidates available with today's technology. However, slow response and insufficient nonlinearity can impose limitations for many potential applications. The requirement for speed may become especially important in proportion to the number of elements which have to be addressed in a device. This may result in increasingly impractical production costs for the potential use of such devices in flat-panel displays for use in video terminals, oscilloscopes, radar and television screens.

It has been shown by N. A. Clark and S. T. Lagerwal in Appl. Phys. Lett. 36: 899 (1980) and in U.S. Pat. No. 4,367,924 that electro-optic effects with submicrosecond switching speeds are achievable using the technology of ferroelectric liquid crystals (FLCs). Some display structures prepared using FLC materials, in addition to the high speed (about 1,000 times faster than currently used twisted nematic devices) reported by these investigators, also exhibit bistable, threshold sensitive switching, making them potential candidates for light modulation devices including matrix addressed light valves containing a large number of elements for passive displays or graphic and pictorial information, as well as for optical processing applications.

Smectic C liquid crystal phases composed of chiral, nonracemic molecules possess a spontaneous ferroelectric polarization, or macroscopic dipole moment, deriving from a dissymmetry in the orientation of molecular dipoles in the liquid crystal phases (Myer et al. (1975) J. Phys. (Les Ulis, Fr) 36:L-69). The ferroelectric polarization density is an intrinsic property of the material making up the phase and has a magnitude and sign for a given material under a given set of conditions. In ferroelectric liquid crystal display devices, like those of Clark and Lagerwal, appropriate application of an external electric field results in alignment of the molecules in the ferroelectric liquid crystal phase with the applied field. When the sign of the applied field is reversed, realignment or switching of the FLC molecules occurs. This switching can be employed for light modulation. Within a large range of electric field strengths, the switching speed (optical rise time) is inversely proportional to applied field strength and polarization or dipole density (P), and directly proportional to orientational viscosity. High switching speeds are then associated with FLC phases which possess high polarization density and low orientational viscosity.

A basic requirement for application of ferroelectric liquid crystals in such devices is the availability of chemically stable liquid crystal compounds or mixtures which exhibit ferroelectric phases (chiral smectic C) over a substantial temperature range about room temperature. In some cases, the ferroelectric liquid crystal compound itself will possess an enantiotropic or monotropic ferroelectric (chiral smectic C*) liquid crystal phase. Ferroelectric liquid crystal mixtures possessing chiral smectic C* phases with useful temperature ranges can also be obtained by admixture of chiral, nonracemic compounds, designated ferroelectric liquid crystal dopants into liquid crystal host material (which may or may not be composed of chiral molecules). Addition of the dopant can affect the ferroelectric polarization density and/or the viscosity of the C* phase and thereby affect the switching speed. Desirable FLC dopants are molecules which impart high ferroelectric polarization density to an FLC material without significantly increasing the orientational viscosity of the mixture.

Thermotropic liquid crystal molecules typically possess structures which combine a rigid core coupled with two relatively "floppy" tails (see Demus et al. (1974) Flussige Kristalle In Tabellen, VEB Deutscher Verlag fur Grundstoffindustrie, Lebzig for a compilation of the molecular structures of LC molecules). FLC materials have been prepared by the introduction of a stereocenter into one of the tails, thus introducing chirality. The first FLC compound to be characterized was DOBAMBC (Meyer et al., supra) which contains a 2-methylbutyl chiral tail. Pure DOBAMBC exhibits a smectic C* phase with a ferroelectric polarization of $-3$ nC/cm$^2$. The structures and polarization of several known smectic C* materials, including several containing phenyl benzoate cores, have been summarized in Walba et al. (1986a) J. Amer. Chem. Soc. 108: 5210-5221, which also discusses a number of empirical correlations between molecular structure and FLC properties. This reference also reports the synthesis and properties of FLC compounds which contain nonracemic 2-alkoxy-1-propoxy tail units, derived from lactic acid, coupled to p-alkoxy phenyl benzoate cores. These compounds, also the subject of U.S. Pat. No. 4,556,727, possess monotropic smectic C* phases which display fast switching speeds at room temperature. It is also reported therein that certain eutectic mixtures containing these FLC compounds possess thermodynamically stable or entaniotropic smectic C* phases with high polarization density and fast electro-optical switching speeds. U.S. Pat. No. 4,556,727 discloses that the attachment of an enantiomerically enriched lactic acid derived tail unit to the para position of the phenyl group of a phenyl benzoate core unit will confer the desired properties of large ferroelectric dipole density and low orientational viscosity to a chirally asymmetric liquid cyrstal compound. The disclosure of that patent relates to ferroelectric smectic liquid crystals of the following general formula:

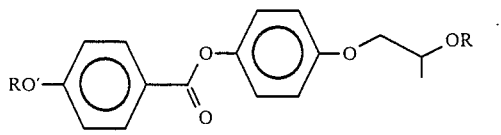

wherein R is a lower alkyl group containing one to three carbon atoms and R' is an alkyl group containing nine to twelve carbon atoms.

In related work, Walba et al. (1986) J. Amer. Chem. Soc. 108: 7424–7425 and Walba and Vohra, U.S. Pat. No. 4,648,073 disclose ferroelectric (chiral) smectic liquid crystal compounds having an achiral core and chiral tail units derived from (2,3)-alkyloxiranemethanols which possess a high ferroelectric polarization density. The ferroelectric crystal materials reported have the following general formulas:

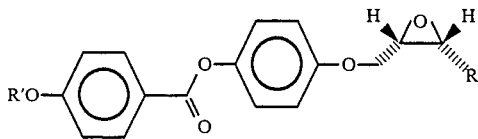

where R is an alkyl of one to seven carbon atoms and R' is an alkyl of five to twelve carbon atoms.

Additional related work, Eidman and Walba, U.S. patent application Ser. No. 800,851, filed July 1, 1986, discloses chirally asymmetric liquid crystals possessing the phenyl benzoate core unit and 1-cyanoalkoxy chiral tails.

Also related is the subject matter of Walba and Razavi, U.S. patent application Ser. No. 911,096, filed Sept. 24, 1986, which discloses chirally asymmetric compounds possessing an achiral (phenyl benzoate) core unit with 1-fluoro or 1-chloroalkyl group chiral tail units having the general formula:

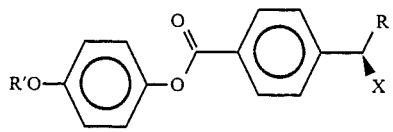

wherein R is an alkyl group of three to twelve carbon atoms, R' is an alkyl of five to twelve carbon atoms, and X is a chlorine atom or a fluorine atom. These materials impart the property of high polarization density in admixtures which display an FLC phase and are useful as FLC dopants.

While several useful ferroelectric liquid crystal materials (both pure compounds and mixtures) have thus been reported, optimum response times have not been achieved (theoretical limit estimated as 10–50 nsec, Walba et al. (1986a), (supra). For this reason, new FLC materials particularly those having high polarization density and low viscosity are desirable, as are new FLC dopants which can impart desired properties to FLC materials.

SUMMARY OF THE INVENTION

The present invention provides a class of chirally asymmetric molecules which are useful as components of ferroelectric liquid crystal materials. These compounds can impart the properties of high ferroelectric polarization density and fast electro-optical switching speeds on low polarization materials when mixed with such materials to form ferroelectric liquid crystal compositions. Alternatively, certain of the compounds of the present invention in pure form can also possess stable smectic C* phases having high polarization density.

The compounds of the present invention are prepared by the incorporation of enantiomerically enriched 2,3-epoxy alkyl or 1-halo-2,3-epoxy alkyl tails, as in formulas I and II into a suitable liquid crystal core, such as those cores based on a phenyl- or biphenylbenzoate structure. More specifically, attachment of enantiomerically enriched 2,3-epoxy alkyl or 1-halo-2,3-epoxy alkyl tails to the para position of phenyl- or biphenylbenzoate core units results in compounds which are useful in the preparation of ferroelectric liquid crystal materials, either in pure form or as a component in an FLC mixture.

An important feature of the present invention is the finding that the 1-haloepoxy compounds of formula IIA have much higher extrapolated polarization densities than those of the analogous diastereomers of formula IIB. This effect is believed to result from the relative alignment of the epoxide and halogen bond dipoles in the preferred conformation of the diastereomers in the FLC phase.

Specifically the present invention provides compounds of the formula:

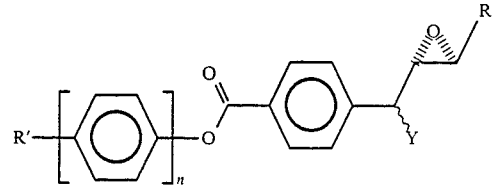

wherein Y is H, F, Cl or Br and wherein n is 1 or 2, R' is an alkyl or alkoxy group containing three to fifteen carbon atoms and R is an alkyl group containing three to fifteen carbon atoms. The alkyl and alkoxy groups may be straight chain or branched, including but not limited to n-propyl, isopropyl, n-butyl, isobutyl, sec-butyl, t-butyl, n-pentyl, n-hexyl, n-heptyl, n-octyl, n-nonal, n-decyl, n-undecyl, or n-dodecyl, as well as the various isomers or alkoxy groups thereof. Compounds having a phenyl- or biphenylbenzoate core wherein R' is an alkyl or alkoxy group containing five to twelve carbons and R is an alkyl group containing five to twelve carbon atoms are preferred, and compounds wherein R' is n-decyloxy and R is n-hexyl are more preferred. For compounds of the present invention containing a phenyl benzoate core, wherein N=1 and Y=H, F, Cl or Br, R' is an alkyl or alkoxy group containing three to fifteen carbon atoms and R is an alkyl group containing three to fifteen carbon atoms. Phenylbenzoates (N=1) wherein Y=H, F, Cl or Br and wherein R' is an alkyl or alkoxy group containing five to twelve carbon atoms and R is an alkyl group containing five to twelve carbon atoms are preferred, and phenylbenzoates wherein R' is n-decyloxy and R is n-hexyl are most preferred. For epoxy halides of the present invention compounds wherein Y is F or Cl are preferred.

In a particular embodiment of the present invention, 1-haloepoxides having the structure of formula IIA are provided, wherein X is a F, Cl or Br, n is 1 or 2, R' is an alkyl or alkoxy group containing three to fifteen carbon atoms and R is an alkyl group containing three to fifteen carbon atoms. Compounds of formula IIA having a phenyl- or biphenylbenzoate core wherein R' is an alkyl or alkoxy group containing five to twelve carbons and R is an alkyl group containing five to twelve carbon atoms are preferred, and compounds wherein R' is n-decyloxy and R is n-hexyl are more preferred. For compounds of formula IIA (wherein X=F, Cl or Br) which are phenylbenzoates (N=1), R' is an alkyl or alkoxy group containing three to fifteen carbon atoms and R is an alkyl group containing three to fifteen carbon atoms. Phenylbenzoates (n=1) of formula IIA wherein R=F, Cl or Br and wherein R' is an alkyl or alkoxyl group containing five to twelve carbon atoms and R is an alkyl group containing five to twelve carbon atoms are preferred, and phenylbenzoates wherein R' is n-decyloxy and R is n-hexyl are most preferred. For epoxy halides of formula IIA, compounds wherein X=F or Cl are preferred.

In a second aspect, the present invention provides chirally asymmetric intermediate compounds which are useful in the synthesis of ferroelectric liquid crystal compounds or components. The synthetic intermediates of the present invention are chiral epoxy alcohols, as in formula VII. These compounds are important in the synthesis of chiral FLC epoxides of formula I (via deoxygenation) and in the synthesis of the FLC haloepoxides of formula II (via halogenation) chiral.

Specifically, the present invention provides epoxy alcohols of the formula VII wherein n=1 or 2 and wherein R' is an alkyl or alkoxyl group containing three to fifteen carbon atoms and R is an alkyl group containing three to fifteen carbon atoms. Intermediates in which R' is an alkyl or alkoxyl group containing five to twelve carbon atoms and R is an alkyl group containing five to twelve carbon atoms are preferred, and intermediates in which R' is decyloxy and R is hexyl are more preferred. Intermediates containing a phenylbenzoate core where n=1 are preferred.

DETAILED DESCRIPTION OF THE INVENTION

The ferroelectric liquid crystal compounds of the present invention are prepared according to the following general reaction scheme:

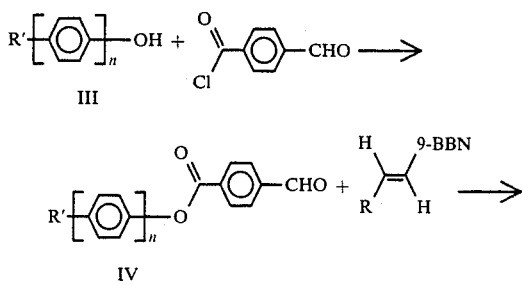

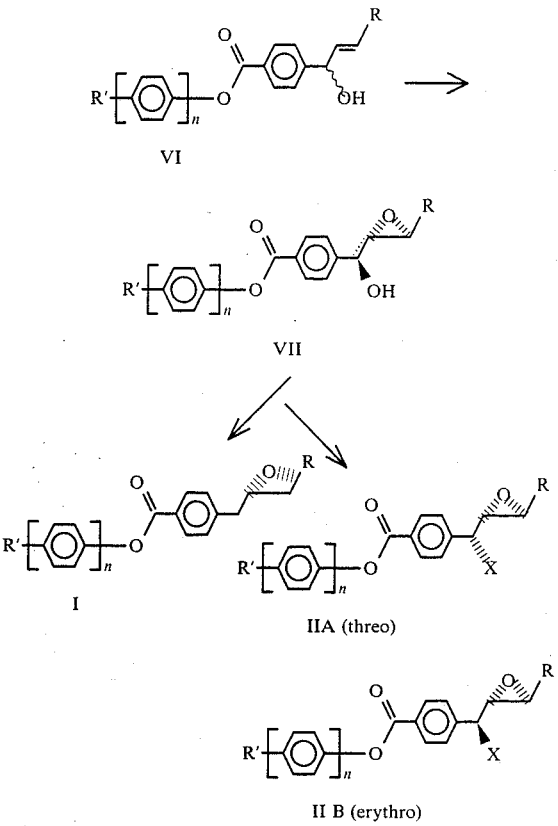

where X=F, Cl or Br.

In general terms compounds of formula I are prepared by deoxygenation of the enantiospecific intermediate epoxy alcohols of formula VII by a modification of the Barton procedure (Robbins et al. (1983) J. Amer. Chem. Soc. 105: 4059; Barton and McCombie (1975) J. Chem. Soc. Perkins Trans. 1: 1574). The epoxy alcohols (VII) in turn are prepared via an enantioselective epoxidation (Martin et al. (1981) 103: 6237–6240 and Sharpless, U.S. Pat. No. 4,471,130) from the allyl alcohols of formula VI. The allyl alcohols (VI) are synthesized by reaction of the benzaldehydes of formula IV with the B-alkenyl-9-BBN (9-borabicyclo[3.3.1] nonane) of formula V which add across the carbonyl group of the benzaldehyde (Jacob and Brown (1977) J. Org. Chem. 42: 579–580). The benzaldehydes (IV) are prepared by esterification of 4-formylbenzoylchloride with the substituted phenols of formula III.

The 9-BBN derivatives (V) are prepared by a known method by reaction of the appropriate terminal alkyne with 9-BBN (Brown et al. (1979) J. Amer. Chem. Soc. 101: 96–99). For example, B-[(E)-1-octene-1-yl]-9-BBN is prepared by reaction of 1-octyne with 9-BBN. Substituted phenols (III) are either available from commercial sources or are readily prepared by methods known to the art. For example, the preparation of a number of 4-alkoxyphenols is described in Neubert et al. (1978) Mol. Crys. Liq. Cryst. 44: 197–210. Substituted alkoxy biphenols of formula III (where n=2) can be prepared by analogous methods. The 4-decyloxyphenol used in the present work was prepared by the method of Neubert et al., supra. Alkyl phenols and alkyl biphenols of formula III can also be prepared by methods known to the art.

Compounds of formula II, epoxy halides, are also prepared from the intermediate epoxy alcohols (VII). The epoxy halides can be prepared as a mixture of the threo and erhthro diastereomers which can be separated, for example, by silica column chromatography. Alternatively, in most cases, the individual diastereomers can be prepared directly, in isomerically pure form. By appropriate choice of halogenation reagent any of the compounds of formula IIA or IIB, where X is F, Cl or Br can be readily prepared using procedures described herein.

Compounds of formula I, II and VII each represent one of a pair of enantiomers. The pair of enantiomers of each compound will function in an equivalent manner. For illustration, the structure of the enantiomer of the fluoroepoxide (IIA, where n=1, R'=n-decyloxy and R=n hexyl) is shown:

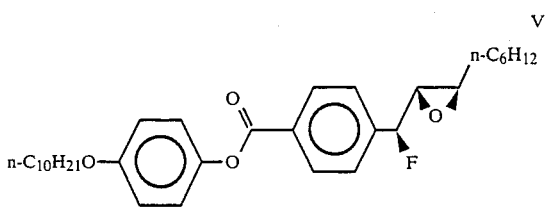

VIII

Compound VIII will function equivalently to its enantiomer of formula IIA in FLC materials, except that the sign of P will be reversed. The enantiomers of compounds of formulas I and II can be prepared from the epoxy alcohol enantiomer of formula VII by the methods described herein. The enantiomers of the epoxy alcohols of formula VII can be prepared by the method of Example 3 replacing the L-tartrate reagent with the analogous D-tartrate reagent.

If the starting materials 4-decyloxyphenol and B-[(E)-1-octene-1-yl]-9-BBN are employed the intermediate epoxy alcohol (VII) and subsequently the epoxide (I) or epoxy halides (II), where R' is n-decyloxy and R is n-hexyl, result.

The liquid crystal properties of the compounds of formula I are illustrated by those of the epoxide I, where N=1, R'=n-decyloxy and R=n-hexyl, which is hereinafter designated W203, while the properties of the epoxy halides of formulas IIA are illustrated by those of fluoro (designated W200) or chloro (designated W210) epoxides of formula IIA where N=1, R'=n-decyloxy and R=n-hexyl and the properties of the epoxy halides of formula IIB are illustrated by those of the fluoro epoxide (designated W199) where n=1, R'=n-decyloxy and R=n-hexyl.

None of the compounds W199, W200, W203 or W210 in pure form possesses an enantiotropic or monotropic ferroelectric (smectic C*) liquid crystal phase. However, when these compounds are mixed with a known FLC host material, such as W82 (formula IX), mixtures possessing ferroelectroic smectic C* phases are produced.

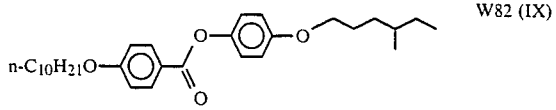

W82 (IX)

Table 1 summarizes the phase transition temperatures, optical rise times and polarization densities of some exemplary mixtures. In Table 1, the phases are noted as X=crystal, I=isotropic liquid, A=smectic A, C*=chiral smectic C, N*=chiral nematic and phase transition temperatures are given in °C. Optical rise times are measured in response to a driving voltage of 15 V/$\mu$m at the temperature given in the table. Polarization densities (P) are given in nC/cm$^2$ and the magnitude of P was measured by integration of the dynamic current response on reversing the applied electric field, as described in Martinot-Lagargde (1976) J. Phys. 37, C-3, p. 129 and Martinot-Lagarde (1977) J. Phys. Lett. 38, L-17.

W82 (IX) is known to possess an enantiotropic ferroelectric C* phase with very low polarization density of the order of 1 nC/cm$^2$ and very low electro-optical switching speed of the order of 3 msec (1 $\mu$m thick layer, SSFLC geometry, 15 V/$\mu$m driving voltage). Mixtures of the compounds of the present invention, particularly compounds W200, W203 and W210, as shown in Table 1, possess ferroelectric C* phases with higher polarization density and or faster switching speeds than W82.

An important aspect of the present invention is the finding that the 1-haloepoxides of formula IIA have properties as FLC dopants significantly different from those of formula IIB. Compounds of formula IIA can impart higher polarization densities in FLC mixtures. This property can be qualitatively compared in the different diastereomers by comparing the polarization densities of the pure diastereomers which can be extrapolated from polarization density measurements in mixtures. The extrapolated P of W199 (formula IIB) is about +25 nC/cm$^2$, while that of W200 (formula IIA) is about −170 nC/cm$^2$. This difference can be discerned physically, since FLC mixtures containing the IIA isomer will display higher polarization densities (P), and higher switching speeds than FLC mixtures containing an equal amount of the corresponding IIB isomer. It is believed that the difference in polarization densities of IIA and IIB isomers is due to the relative alignment of the epoxide and halogen bond dipoles in the preferred configuration of the isomers within the FLC phase. With the IIA isomers the dipoles are aligned in the same direction with respect to the smectic tilt plane, while in the IIB isomers the dipoles are opposed, resulting in the higher polarization density of the IIA isomer. The relationship between dipole alignment and ferroelectric polarization density has been discussed for related molecules in Walba et al. (1986a), and Walba et al. (1986b), supra. The difference in polarization between isomers of formula IIA and IIB is general and qualitatively independent of X and the structure of the core.

Variation in the structure of the cores and length and degree of branching in the R and R' groups of compounds encompassed in formulas I and II can affect the liquid crystal properties of the pure material or mixtures containing them. For example, some of the compounds of the present invention may possess smectic C* phases while others do not and the characteristics of any such smectic C* phases (i.e. stability, temperature range) may vary.

TABLE 1
Properties of FLC mixtures

| Mixture | Phase Sequence | τ_r μsec | Temp. °C. | P nC/cm² |
|---|---|---|---|---|
| W203 (34%) + W82 | X ←43→ C* ←56→ N* ←60→ I | 67 | 43 | |
| W199 (7.37%) +W82 | X →53→ C* ←66→ A ←70→ I<br>X ←40← C* | | 40 | +2 |
| W199 (31%) in W82 | C* ←58← A ←59← N* ←65← I | 90 | 37 | |
| W200 (7.58%) in W82 | X →25→ C* ←61.3→ A ←66→ I | 76 | 28 | −13 |
| W210 (18%) in W82 | X →40→ C* →50→ A →61-70→ I<br>←46← A ←56-58← I | 130 | 25 | −15 |

EXAMPLE 1

This example illustrates the procedure for synthesizing benzaldehydes of formula IV by condensation of an alkoxyphenol (III) with 4-formylbenzoylchloride.

A 1 l flame dried flask equipped with a magnetic stirring bar and a syringe septum was charged with 14 g of 4-decyloxyphenol (55.91 mmole), 9.45 g of 4-formylbenzoylchloride (56.06 mmole) and 0.82 g of 4-pyrrolidinopyridine in 500 ml of dry tetrahydrofuran (THF). Triethylamine (8.6 ml, 61.70 mmole) was added while stirring vigorously. The reaction mixture was stirred for 1.5 h, after which the amine hydrochloride was filtered off and the filtrate was concentrated. The solid obtained was dissolved in 300 ml of $CH_2Cl_2$ and the solution was then washed sequentially with 75 ml of saturated aqueous $CuSO_4$, 75 ml of 15% (w/v) aqueous NaOH, 75 ml of 10% (v/v) aqueous HCl and 75 ml of saturated aqueous $NaHCO_3$. The washed organic layer was then dried over $Na_2SO_4/K_2CO_3$ and the solvent was removed in vacuo to obtain 29 g of crude product. Recrystallization from 1000 ml 2-propanol and 600 ml of 33% (v/v) ethylacetate/hexanes afforded 15.18 g (71% yield) of 4'-(n-decyloxy)phenyl 4-(formyl)benzoate (IV, where R'=n-decyloxy).

EXAMPLE 2

The following example illustrates the synthesis of allyl alcohols of the formula VI by reaction of benzaldehydes of formula IV with B-[(E)-1-alken-1-yl]-9-BBN, formula V.

A 250 ml flame dried flask equipped with a syringe septum, a condenser and a magnetic stirring bar was charged with 10.93 g of 4'-N-decyloxy)phenyl 4-(formyl)benzoate (28.57 mmole) in 110 ml THF. To this solution, 11.64 g (32.86 mmole) B-[(E)-1-octen-1-yl]-9-BBN (V, where R=n-hexyl) was added dropwise, under argon. The reaction mixture was then stirred at room temperature for 2 h, after which it was brought to reflux and stirred overnight. Ethanolamine (1.98 ml, 32.86 mmole) was then added to the cooled (ice/water) reaction mixture. The cooled reaction mixture was then stirred for 15 m before the solvent was removed. Ether (50 ml) was then added to the reaction concentrate, the mixture was cooled (ice/water) and the resulting solid was filtered through silica gel (1 inch, in a 1½ in filter funnel). The solid was eluted from the silica by washing with 20% (v/v) ethylacetate/hexanes (6×25 ml). The combined filtrates were concentrated in vacuo and the resulting crude product purified by flash chromatography on silica gel by eluting with 20% (v/v) ethylacetate/hexane to afford 10.31 g (73% yield) of the allyl alcohol 4'-(n-decyloxy)phenyl 4-[(E)-2-noneneol]-benzoate (VI, where R'=n-decyloxy and R=n-hexyl).

EXAMPLE 3

This example illustrates the procedure for synthesizing epoxy alcohols of formula VII from the allyl alcohols of formula VI.

A 250 ml flame dried flask equipped with a magnetic stirring bar and a syringe septum was charged with 5.49 g of titanium(IV) isopropoxide (18.44 mmole) in 100 ml of $CH_2Cl_2$. The solution was cooled to −30° C. while stirring under argon. (+)-diisopropyl L-tartrate (4.65 ml, 22.11 mmole) was then added to the flask and the mixture was stirred for 20 m. A cold ($CCl_4$/dry ice) solution of 4'-(n-decyloxy)phenyl 4-[(E)-2-noneneol]benzoate (9.12 g, 18.44 mmole) in 50 ml $CH_2Cl_2$ was then added to the reaction flask. An additional 34 ml of $CH_2Cl_2$ was used to wash in any residual allyl alcohol. The cooled reaction mixture was then stirred for 10 m after which 3.32 ml of t-butyl hydroperoxide (2.5M in toluene, 8.3 mmole) was added. The reaction mixture was then placed in a freezer for 18 h. A solution of ferrous sulfate (9.22 g) and tartaric acid (3.7 g) in 37 ml of water was prepared and cooled (ice/water). The cooled solution was then added to the reaction mixture and the mixture was warmed to room temperature and stirred for 1 h. The aqueous and organic solvent layers were separated and the aqueous layer was washed with ether (3×50 ml). The ether washings were combined with the organic layer, which was then dried over $NaSO_4$. Solvent was removed in vacuo and the resulting oil was dissolved in a minimum amount of 20% (v/v) ethylacetate/hexanes. This solution was filtered through silica (2 inches) which was washed thoroughly with 20% (v/v) ethylacetate/hexanes. The combined filtrate was concentrated and purified by flash chromatography on silica by eluting with 25% (v/v) ethylacetate/hexanes. Recrystallization of the product from hexanes at −20° C. resulted in a gel. The recrystallization solution was then centrifuged (−20° C.) and the solvent was decanted from the 4'-(n-decyloxy)phenyl 4-[(2S,3S)-3-hexyloxirane-2-(S)methanol]benzoate gel (VII, where R'=n-decyloxy and R=n-hexyl; 3.73 g, 88% yield).

EXAMPLE 4

This example illustrates the need for synthesizing expoxides of formula I by reduction of epoxy alcohols of formula VII A flame dried 10 ml flask equipped with a magnetic stirring bar and a syringe septum was charged with 0.5 g of 4'-(n-decyloxy)phenyl 4-[(2S,3S)-3-hexyloxirane-2-(S)methanol]benzoate (0.98 mmole) and 0.24 g of DMAP, dimethylaminopyridine, (1.96 mmole) in 6 ml of $CH_2Cl_2$. Phenyl chlorothionocarbonate (0.18 ml, 1.3 mmole) was then added by syringe under argon. The reaction mixture was stirred overnight. The reaction mixture was diluted with an additional 10 ml of $CH_2Cl_2$ and was then washed sequentially with 10 ml of water, 10% (v/v) HCl (3×10 ml) and 10 ml of brine. The organic layer was then dried over Na₂SO₄ and the solvent was removed in vacuo. The resulting oil was purified by flash chromatography by eluting with 11% (v/v) ethylacetate/hexanes to yield 0.61 g (97% yield) of the phenyl thionocarbonate 4-[(2S,3S)-3-hexyloxirane-2-(S)-methyl phenyl thionocarbonate] benzoate as a clear colorless oil.

A flame dried, 10 ml three neck flask equipped with a magnetic stirring bar, a condenser and a syringe septum was charged with 0.062 g of 4-[(2S,3S)-3-hexyloxirane-2-(S)-methyl phenyl thionocarbonate]benzoate (0.097 mmole), 0.13 ml of tributyltin hydride (0.48 mmole) and 0.002 g of AIBN, azobis isobutyronitrile, (0.001 mmole) in 1 ml of distilled toluene. The reaction mixture was degassed with argon (20 m) prior to heating (75° C., 1.5 h with stirring). The volatiles were then removed in vacuo, and the product residue was purified by flash chromatography on silica gel by eluting with 11.5% (v/v) ethylacetate/hexanes. An essentially quantitative yield of the epoxide 4'-(n-decyloxy)phenyl 4-[(2S,3S)-3-hexyloxirane-2-methyl]benzoate (I, where R'=n-decyloxy and R=n-hexyl) was obtained.

EXAMPLE 5

This example illustrates the procedure for synthesizing threo and erythro isomers of epoxy halides of formula II(A and B) from epoxy alcohols of formula VII.

4'-(n-decyloxy)phenyl 4-[(2S,3S)-3-hexyloxirane-2-(S)methanol]benzoate (0.5 g, 0.98 mmole) in 80 ml of CH₂Cl₂ was introduced into a 100 ml flame dried flask equipped with a syringe septum and a stirring bar. The reaction flask was cooled in a dry ice/acetone bath after which 0.13 ml of diethylaminosulfur trifluoride, DAST, (0.98 mmole) was added and the cooled reaction mixture was stirred for 2 h. Water (7 ml) was added to the reaction mixture, which was then warmed to room temperature. A brine solution (10 ml) was added to the mixture and the organic layer was separated from the aqueous layer. The organic layer was washed with 10 ml saturated NaHCO₃ and then dried over K₂CO₃/Na₂SO₄. The solvent was removed in vacuo and the product residue was purified by flash chromatography on silica gel by eluting with 9% (v/v) ethylacetate/hexanes to afford 0.46 g (92% yield) of the epoxy halide 4'-(n-decyloxy)phenyl 4-[(2S,3S)-3-hexyloxirane-2-fluoromethyl]benzoate (II, where R'=n-decyloxy and R=n-hexyl). The product was a mixture of the threo (IIA) isomer (0.11 g; 24%) and the erythro (IIB) isomer (0.35 g; 76%). The amount of erythro isomer produced could be increased to about 50% by doing the DAST reaction at higher temperature (about 0° C.). The epoxy fluoride diasteromers were separated by repeated silica gel chromatography (about 0.5 mg of mixture on a 50 mm×8 in column) employing 9% (v/v) ethylacetate/hexanes as the eluting solvent. About 5–6 passes through the column were required to obtain satisfactory separation. Substitution of thionyl chloride for DAST reagent in this procedure afforded the mixture of epoxy chlorides, which were readily separated by silica gel chromatography.

EXAMPLE 6

This example illustrates a procedure for preparing the threo isomer of the halo epoxides of formula IIA.

A solution of 4'-(n-decyloxy)phenyl 4-[(2S,3S)-3-hexyloxirane-2-(S)methanol]benzoate (0.5 g, 0.98 mmole), triethylamine (0.3 ml, 2.15 mmole) and DMAP (0.05 g) in 2 ml of CH₂Cl₂ was cooled (ice/water). To this cooled, stirred solution, 0.1 ml of methanesulfonyl chloride (1.29 mmole) was added. The mixture was stirred for an additional 20 m after which 20 ml of ether was added to the reaction mixture and the organic layer was washed sequentially with 10% (v/v) HCl (3×10 ml) and 10 ml of saturated NaHCO₃. The washed organic layer was then dried over Na₂SO₄ and the solvent was removed in vacuo to give a quantitative yield of the epoxy mesylate, 4'-(n-decyloxy)phenyl 4-[(2S,3S)-3-hexyloxirane-2-(S)-methanesulfonyl methyl]benzoate.

The epoxy mesylate (0.32 g, 0.54 mmole), LiCl (0.06 g, 1.42 mmole) and 2 drops of 12-crown-4 in dimethylfuran (DMF) was introduced into a 10 ml flame dried flask equipped with a magnetic stirring bar and a syringe septum. The reaction mixture was then stirred for 4 days, under argon. Ether (10 ml) was added to the reaction mixture and the mixture was then poured over 10 ml of ice/water. The solvent layers were separated and the aqueous layer was then washed with ether (6×10 ml). The washings were combined with the organic layer and dried over Na₂SO₄/K₂CO₃ and the solvent was removed in vacuo. The resulting solid was purified by flash chromatography on silica gel by eluting with 9% (v/v) ethylacetate/hexanes yielding 0.22 g (76%) of epoxy chloride, 4'-(n-decyloxy)phenyl 4-[(2S,3S)-3-hexyloxirane-2-(R)-chloromethyl]benzoate (IIA, where R'=n-decyloxy and R=n-hexyl). Attempts to prepare the analogous threo epoxy fluoride by this procedure (LiF substituted for LiCl) were unsuccessful, resulting in opening of the epoxide ring.

The invention has been described and illustrated by reference to several preferred embodiments, but it is not intended to limit the invention by doing so. For example, while as noted above, a single enantiomer of each chirally asymmetric compound has been prepared, it is intended that the invention encompass both enantiomers of each compound. It is also intended that the invention include mixtures of the two enantiomers of the same formula in which there is an excess of one enantiomer. It is further intended that the invention encompasss not only the FLC dopant compounds of formulas I and II, but also compositions or formulations in which these compounds are admixed with each other or with other compounds including LC and FLC materials.

We claim:

1. A compound of the formula:

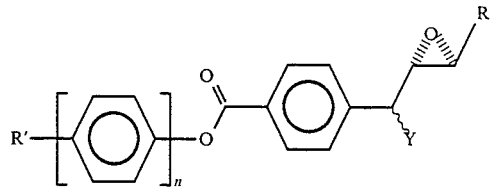

wherein n is 1 or 2, R' is selected from the group consisting of an alkyl group containing three to fifteen carbon atoms and an alkoxy group containing three to fifteen carbon atoms, R is an alkyl group containing three to fifteen carbon atoms and Y is selected from the group consisting of H, F, Cl and Br.

2. The compound according to claim 1 in which Y is H.

3. The compound according to claim 2 in which n is 1.

4. The compound according to claim 3 in which R' is an alkoxy group containing three to fifteen carbon atoms.

5. The compound according to claim 4 in which R' is an alkoxy group containing ten carbon atoms.

6. The compound according to claim 5 in which R' is the n-declyoxy group.

7. The compound according to claim 3 in which R is an alkyl group containing six carbon atoms.

8. The compound according to claim 7 in which R is the n-hexyl group.

9. The compound according to claim 8 in which R' is the n-decyloxy group.

10. The compound according to claim 1 in which Y is a halogen selected from the group consisting of F, Cl and Br.

11. The compound according to claim 10 in which Y is a halogen selected from the group consisting of F and Cl.

12. The compound according to claim 11 in which n is 1.

13. The compound according to claim 12 in which R' is an alkoxy group containing three to fifteen carbon atoms.

14. The compound according to claim 13 in which R' is an alkoxy group containing ten carbon atoms.

15. The compound according to claim 14 in which R' is the n-decyloxy group.

16. The compound according to claim 10 in which R is an alkyl group containing six carbon atoms.

17. The compound according to claim 16 in which R is the n-hexyl group.

18. The compound according to claim 17 in which R' is the n-decyloxy group.

19. The compound according to claim 18 in which Y is F.

20. The compound according to claim 19 in which Y is Cl.

21. A compound of the formula:

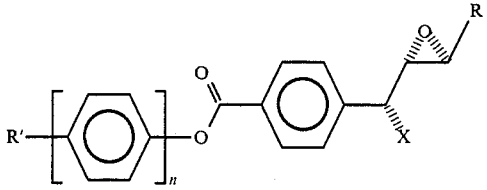

wherein X is a halogen selected from the group of halogens consisting of F, Cl and Br, n is 1 or 2, R' is selected from the group consisting of an alkyl group containing three to fifteen carbon atoms and an alkoxy group containing three to fifteen carbon atoms and R is an alkyl group containing three to fifteen carbon atoms.

22. The compound according to claim 21 in which X is a halogen selected from the group of halogens consisting of F and Cl.

23. The compound according to claim 22 in which n is 1.

24. The compound according to claim 23 in which R' is an alkoxy group containing three to fifteen carbon atoms.

25. The compound according to claim 24 in which R' is an alkoxy group containing ten carbon atoms.

26. The compound according to claim 25 in which R' is the n-decyloxy group.

27. The compound according to claim 23 in which R is an alkyl group containing six carbons.

28. The compound according to claim 27 in which R is the n-hexyl group.

29. The compound according to claim 28 in which R' is the n-decyloxy group.

30. The compound according to claim 29 in which X is F.

31. The compound according to claim 29 in which X is Cl.

32. An epoxy alcohol of the formula:

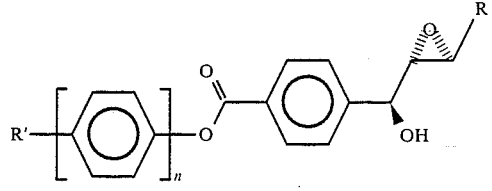

wherein n is 1 or 2, R' is selected from the group consisting of an alkyl group containing three to fifteen carbon atoms and an alkoxyl group containing three to fifteen carbon atoms, and R is an alkyl group containing three to fifteen carbon atoms.

33. The compound according to claim 32 in which n=1.

34. The compound according to claim 33 in which R' is an alkoxy group containing three to fifteen carbon atoms.

35. The compound according to claim 34 in which R' is an alkoxy group containing ten carbon atoms.

36. The compound according to claim 35 in which R' is the n-decyloxy group.

37. The compound according to claim 36 in which R is an alkyl group containing six carbon atoms.

38. The compound according to claim 37 in which R is the n-hexyl group.

39. The compound according to claim 38 in which R' is n-decyloxy.

* * * * *

UNITED STATES PATENT AND TRADEMARK OFFICE
CERTIFICATE OF CORRECTION

PATENT NO. : 4,835,295

DATED : May 30, 1989

INVENTOR(S) : David M. Walba and Homaune A. Razzavi

It is certified that error appears in the above-identified patent and that said Letters Patent is hereby corrected as shown below:

Cover page, in the "Other Publication" section, replace "1087424-7425" with --108:7424-7425--. Column 1, line 46, replace "Lagerwal" with --Lagerwall--. Column 2, line 2, replace "Lagerwal" with --Lagerwall--; column 2, line 12, replace "High" with --Fast--; column 2, line 44, replace "Meyer" with --Myer--; column 2, line 62, replace "entaniotropic" with --enantiotropic--. Column 3, line 2, replace "cyrstal" with --crystal--; column 3, first formula, replace "RO'" with --R'O--; column 3, line 24, replace "formulas" with --formula--. Column 4, line 17, insert --,-- after "II"; column 4, line 61, replace "N=1" with --n=1--. Column 7, line 4, replace "erhthro" with --erythro--; column 7, line 17, replace "n hexyl" with --n-hexyl--; column 7, line 39, insert --,-- after "employed". Column 8, line 18, replace "low" with --slow--; column 8, line 41, replace "higher" with --faster--. Column 9, Table 1, last line, move the line to the right so that the "A" and "I" are aligned with those same letters in the previous line of the Table. Column 10, line 59, insert --.-- after "VII". Column 11, line 48, replace "R'32" with --R'=--. Claim 6, line 2, replace "n-declyoxy" with --n-decyloxy--.

Signed and Sealed this

Twenty-second Day of May, 1990

Attest:

HARRY F. MANBECK, JR.

Attesting Officer     Commissioner of Patents and Trademarks